United States Patent [19]

Harris

[11] Patent Number: 4,461,995
[45] Date of Patent: Jul. 24, 1984

[54] COOLING METHOD AND APPARATUS FOR EDDY CURRENT FLAW DETECTION

[75] Inventor: Richard M. Harris, North Royalton, Ohio

[73] Assignee: Republic Steel Corporation, Cleveland, Ohio

[21] Appl. No.: 316,316

[22] Filed: Oct. 29, 1981

[51] Int. Cl.³ ............... G01R 33/12; G01N 27/90
[52] U.S. Cl. ................................. 324/224; 165/47; 165/DIG. 5; 324/226; 324/240; 336/57
[58] Field of Search ............... 324/224, 226, 239–241, 324/262; 165/47, DIG. 5; 336/57

[56] References Cited

U.S. PATENT DOCUMENTS

| 2,855,565 | 10/1958 | Enders | 324/224 |
| 2,950,094 | 8/1960 | Garmy | 165/47 X |
| 3,234,457 | 2/1966 | Sower | 324/241 |
| 3,303,691 | 2/1967 | Beaujard | |
| 3,694,735 | 9/1972 | Mester | 324/226 |
| 3,872,379 | 3/1975 | Brooks et al. | 324/224 X |
| 3,916,301 | 10/1975 | Vild et al. | 324/233 X |
| 4,024,470 | 5/1977 | Vild et al. | 324/224 |
| 4,101,832 | 7/1978 | Baker | |
| 4,123,708 | 10/1978 | Vild et al. | 324/224 |
| 4,127,815 | 11/1978 | Vild et al. | 324/241 |

FOREIGN PATENT DOCUMENTS 12790 1/1979 Japan ............... 324/224

OTHER PUBLICATIONS

Lennemann et al., Cooling of a Voice Coil Motor for Disk Storages, *IBM Technical Disclosure Bulletin*, vol. 15, No. 9, Feb. 1973, pp. 2873–2874.

Primary Examiner—Gerard R. Strecker
Attorney, Agent, or Firm—Watts, Hoffmann, Fisher & Heinke Co.

[57] ABSTRACT

An eddy current system and method is disclosed for detecting flaws in hot pipe product. The system includes a detector test head (22) having a heat shield (24) defining a generally cylindrical inner wall through which the pipe passes longitudinally. The test head includes structure (50, 62, 64) for spirally directing water onto the inside surface without contacting the hot pipe as it passes through the heat shield. Debris is thereby removed from the space between the shield and the pipe, and the test head is effectively cooled and shielded from the heat of the pipe. Where the pipe is heated above its Curie temperature, such that the pipe is rendered non-magnetic, no normally required saturation coil is needed to magnetically saturate the pipe for eddy current testing, because the coolant flowing over the inner wall cools the test head but does not lower pipe temperature below the Curie point.

22 Claims, 14 Drawing Figures

COOLING METHOD AND APPARATUS FOR EDDY CURRENT FLAW DETECTION

DESCRIPTION

1. Technical Field

The present invention relates to hot pipe flaw detection and more particularly to an improved method and apparatus for liquid cooling and flushing of eddy current flaw detection equipment.

2. Background Art

In the manufacture of metal products such as pipe, it is desirable to inspect for flaws or imperfections as the product is manufactured. According to current manufacturing techniques, some inspection is done by or with the assistance of some type of automated detecting apparatus. Several widely used testing techniques utilize eddy current flaw detectors.

In one type of eddy current detector, an oscillating power source energizes an excitation coil for inducing eddy current flow in a workpiece under inspection. A detection assembly including detection, or probe, coils, as well as the exciter coil, is positioned in proximity to the workpiece and relative movement imparted between workpiece and assembly. Flaws are sensed by the detection coils' response to variation in the eddy current flow due to inhomogeneity in the flawed region. As flaws are located their positions are marked and typically steps are also undertaken to prevent further flaws from occurring.

In a typical system each detector assembly has one or more detecting coils, and both these and the exciter coil are inductively coupled with the workpiece. The exciter coil induces eddy currents, as noted above. The detection coils produce distinctive output signals in response to variations in eddy current flow within the workpiece. These variations are caused by flaws, such as cracks, in the workpiece which interfere with eddy current flow to an extent related to the severity (length and depth) of the flaw. Accordingly, variations in output signals from a detection coil can be correlated to the existence, length and depth of flaws in the workpiece.

Eddy current testing systems have been used to monitor some welded steel pipe or bar stock immediately after manufacture while still hot, which is desirable, for reasons explained below. Because of overheating of eddy current test apparatus, caused by the hot product, some steel pipe could not be inspected while hot.

It is particularly advantageous to inspect the pipe as soon as possible after manufacture. With present high speed pipe fabricating machinery, welded pipe can be produced at speeds of the order of 1,600 ft. of pipe per minute. If a pipe welder is malfunctioning, causing flaws in the product, and the pipe cannot be inspected before cooling, literally miles of defective pipe may be fabricated before flaw inspection techniques reveal the existence of the malfunction in the welder.

The inspection apparatus disclosed in U.S. Pat. No. 4,024,470, to Vild et al, issued May 17, 1977, under the title "Eddy Current Detector for Hot Test Process Having Coolant Fluid and Purge Features" provided a hot pipe inspection technique unknown in the earlier art. This patent has been assigned to the Republic Steel Corporation, assignee of the present invention and is expressly incorporated now by reference.

Apparatus disclosed in U.S. Pat. No. 4,024,470 overcame difficulties experienced in prior art eddy current testers by using water to both cool the detection apparatus and purge from the detector debris, such as scale and dirt, which accumulates during testing. Although representing a significant advancement in the art, use of the apparatus disclosed in U.S. Pat. No. 4,024,470 gave rise to unexpected difficulties, especially with relatively small diameter pipe, which previously had been the easiest to test while hot.

As pointed out in the Vild et al patent, typical prior art inspection apparatus included both an exciter coil and a saturation coil which surrounded a workpiece path of travel. The saturation coil magnetically saturated the workpiece to improve the sensitivity of the eddy current testing. It was found, however, that if a steel pipe is tested at a temperature above its Curie point, (approximately 1415° F. for carbon steel) the saturation coil can be eliminated because the pipe is no longer magnetic. Thus, it was found that eddy current test apparatus could be significantly simplified if appropriate steps were taken to test at a temperature above the Curie point.

The purging and cooling techniques disclosed in the Vild et al patent involve directing water onto the pipe in the vicinity of the test head assembly. This was an effective technique for flushing debris from the vicinity of the test head, but it has also been discovered that sometimes application of the flushing water caused localized cooling of the pipe to a temperature below the Curie point. When this occurred the eddy current tester output signals became noisy and the utility of the eddy current test was impaired. The Vild et al apparatus is thus effective in cooling the eddy current coil assembly and in removing debris from the sensitive area of the coil assembly but unfortunately can cause an unexpected loss in testing effectiveness by cooling the steel workpiece below its Curie point.

Another problem with the device of U.S. Pat. No. 4,024,470 was that the coolant was forced through a partially closed annular chamber defined by structure in the test assembly between the coils and the pipe. The pressure of this chamber necessitated a pipe to coil spacing large enough to accommodate the structure, which spacing limited test sensitivity.

DISCLOSURE OF INVENTION

The present invention provides for fluid purging and cooling of eddy current hot pipe testing apparatus while assuring against undesirable cooling of the pipe workpiece itself. The apparatus enables hot pipe testing without the necessity for providing a saturation coil, inasmuch as a properly cooled and purged test head is provided which does not also reduce hot pipe workpiece temperature below its Curie point.

According to a general aspect of the invention, the invention comprises apparatus for testing hot metallic pipe product which is moved longitudinally along a path with respect to the testing apparatus. The apparatus includes a shielding sleeve surrounding the path and configured and positioned for non-contacting movement of the pipe relative to the sleeve. An eddy current unit is mounted outside the sleeve proximate the workpiece for testing pipe moving through the sleeve. The sleeve is configured to define ports or apertures in its walls adapted for communication with a source of coolant fluid. The ports are oriented non-radially with respect to the pipe for directing fluid flow substantially exclusively onto the interior surface of the shield.

The present invention thus provides for directing coolant fluid onto the interior surface of the shield, but substantially without impingement on the hot workpiece being tested. The apparatus according to this invention provides for cooling of the eddy current detection unit and of the heat shield member, and for purging or flushing from the inside of the shielding sleeve material such as scale and other debris, which accumulates during testing. All this is accomplished without appreciably lowering the temperature of the workpiece, such that, where the hot pipe enters the testing unit at above its Curie temperature, the need for a saturation coil is obviated.

In accordance with a more specific aspect of the present invention, the test head assembly includes a generally tubular shield member defining an inner surface sufficiently large to accommodate passage of the pipe workpiece therethrough, and encircling the path of the pipe. An eddy current detection coil is located outside, but proximate, the inner tubular structure, as is an exciter coil for inducing eddy currents in the workpiece. Both the excitation and the detection of eddy current flow is conducted by means of electromagnetic energy passing through the inner tubular structure between the coils and the pipe workpiece moving through the test head assembly. Housing structure, in cooperation with the inner structure, encloses the coils within a generally annular chamber.

The housing structure defines an inlet channel suitable for communicating with a source of coolant fluid for pumping the coolant into the chamber to effect cooling of the coils located within the chamber. The inner member defines outlet ports or apertures communicating between the inside of the chamber and the interior region of the shield.

The apertures defined by the inner member are oriented to direct coolant fluid from the chamber into the interior region of the shield, in a direction which is nonradial with respect to the pipe workpiece passing through the test assembly.

More specifically, and in accordance with a preferred embodiment of the invention, the apertures in the shield direct fluid about the inner surface of the shield in a direction which is approximately tangential with respect to that inner surface. In this way, fluid exiting from the chamber through the shield apertures is induced to flow in a generally spiral flow path along the interior surface, until reaching one end of the shield, at which point it exits the shield.

This preferred embodiment can thus be seen to direct coolant flow along the inner surface of the shield, with substantially no impingement of the coolant on the pipe workpiece itself. The pipe remains in a hot condition, above its Curie temperature, during testing, while the test assembly is purged and kept relatively cool by the coolant flow. Additionally, the flow of coolant about the interior surface of the shield enhances heat shielding of the test apparatus from the hot workpiece passing through it.

In the preferred embodiment, the test head includes a generally cylindrical stainless steel inner heat shield which surrounds a portion of a pipe test path and has an inside diameter larger than the outside diameter of the pipe to be tested. Accordingly, the shield defines a passageway for a pipe being tested. The shield also defines apertures through which water flows to cool the inner surface of the shield and remove debris and foreign matter from the vicinity of the detection coils without significantly contacting the pipe and thereby reducing its temperature.

Preferably the coolant flow of the present invention is utilized in conjunction with an eddy current coil assembly comprising a plurality of eddy current detection coils and a singular annular excitation coil. Both excitation coil and detection coils are mounted within a chamber defined by the heat shield and housing structure and containing potting compounds.

The preferred test head housing structure includes two end plates spaced apart from each other and attached to the heat shield. One end plate has a fitting for receiving the coolant and directing it to a longitudinal bore in potting compound located around the coil assembly. A radially extending passage connects the bore with an annular coolant distributor region adjacent the heat shield which communicates with the spiral flow apertures. These apertures comprise bores formed through the shield.

Thus, the water enters the distribution region from the potting compound bore and flows through the test head passage to exit through the apertures in a moving spiralling pattern along the inner surface of the shield. This pattern results in the maintenance of a spiralling sheet of coolant encircling the pipe over the entire inner surface without touching the pipe itself. Centrifugal force maintains the coolant in contact with the heat shield as it spirals about the pipe.

The novel flow pattern produced so effectively cools and shields the inner member that the annular chamber between the detector coils and the heat shield, as taught in U.S. Pat. No. 4,024,470 has been eliminated. Elimination of the annular flow chamber permits the detector to workpiece distance to be reduced and thereby enhances detector performance.

From the above it is apparent that one feature and object of the present invention is the provision of method and apparatus aimed at both cooling an eddy current test head and removing debris from the vicinity of the test head while avoiding deleterious temperature reductions of the workpiece being tested. This and other advantageous features achieved through practice of the present invention will become better understood when the accompanying drawings are considered in conjunction with the detailed description which follows.

BEST MODE FOR CARRYING OUT THE INVENTION

Figure 1:
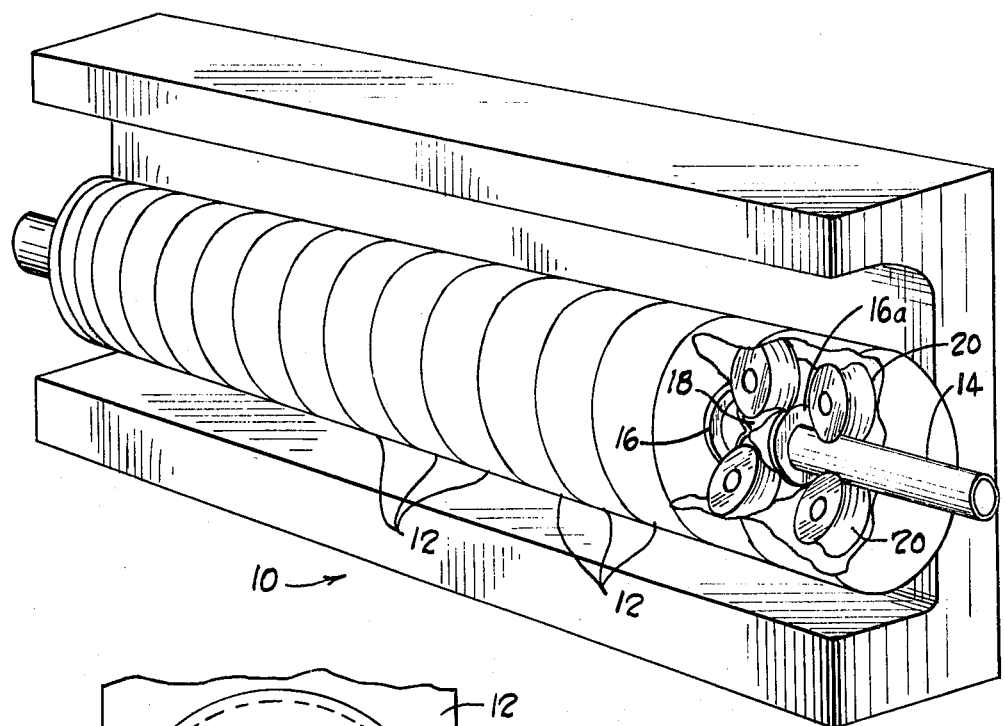
FIG. 1 is a partially sectioned perspective view of a pipe processing station including pipe flaw detection apparatus.
Figure 2:
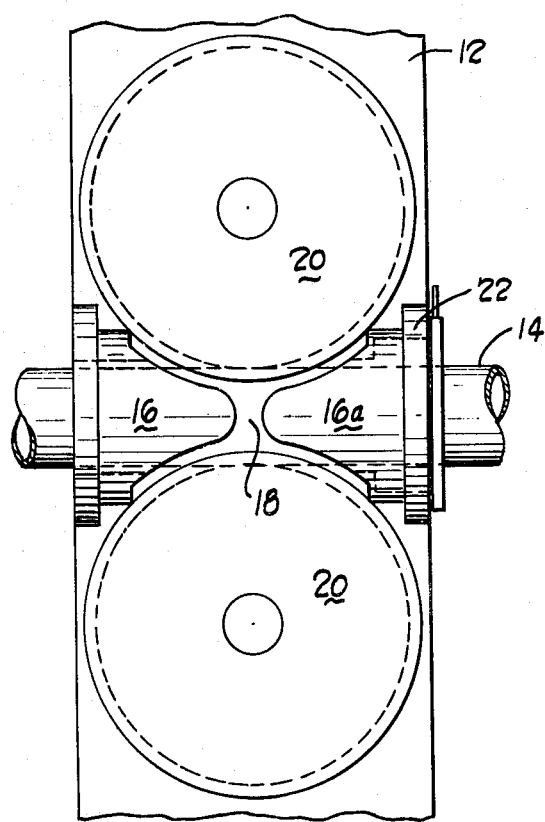
FIG. 2 is a schematic elevation view of a detector test head mounted about a pipe.
Figure 3:
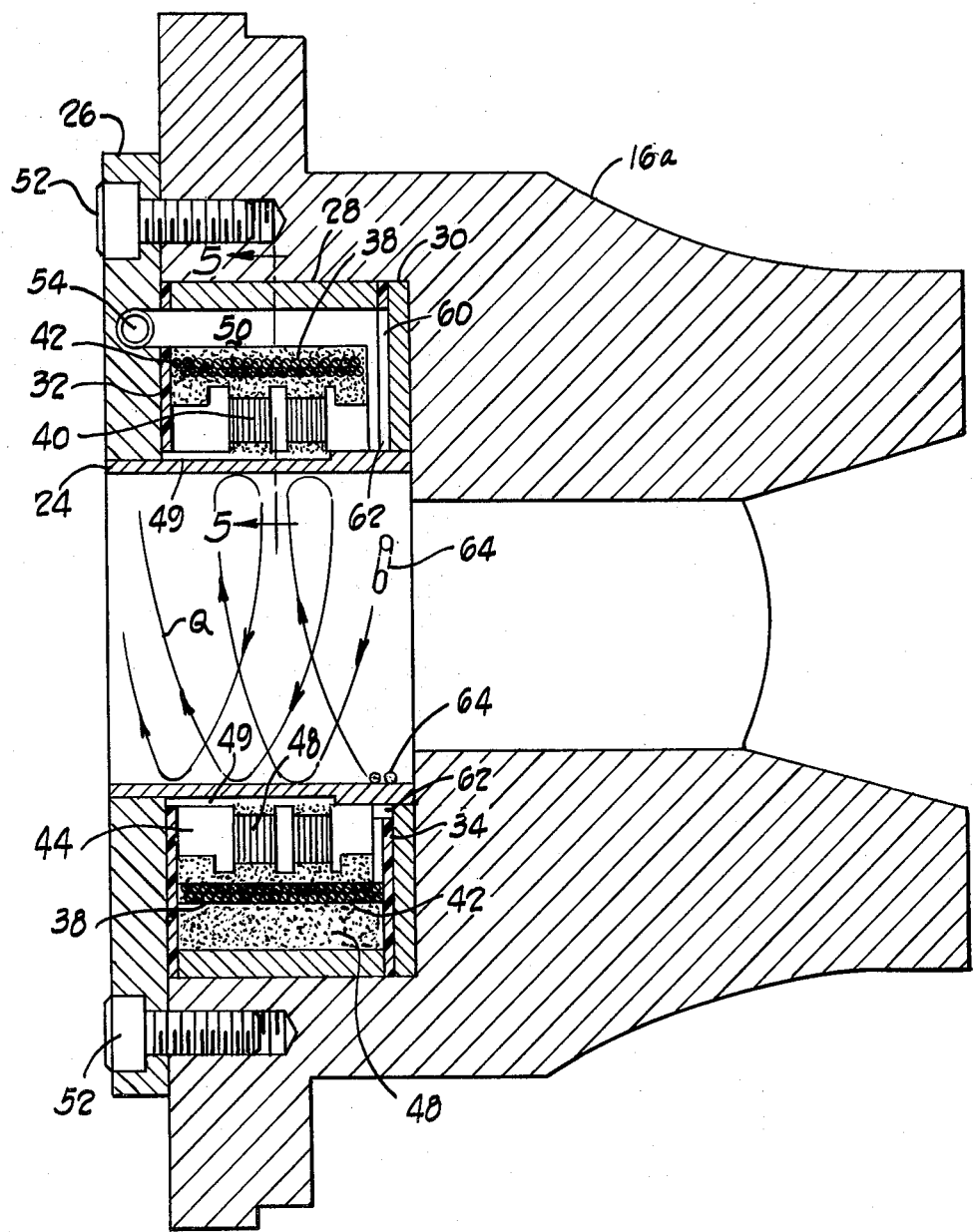
FIG. 3 is a sectioned side elevation view of the test head shown in FIG. 2.
Figure 4:
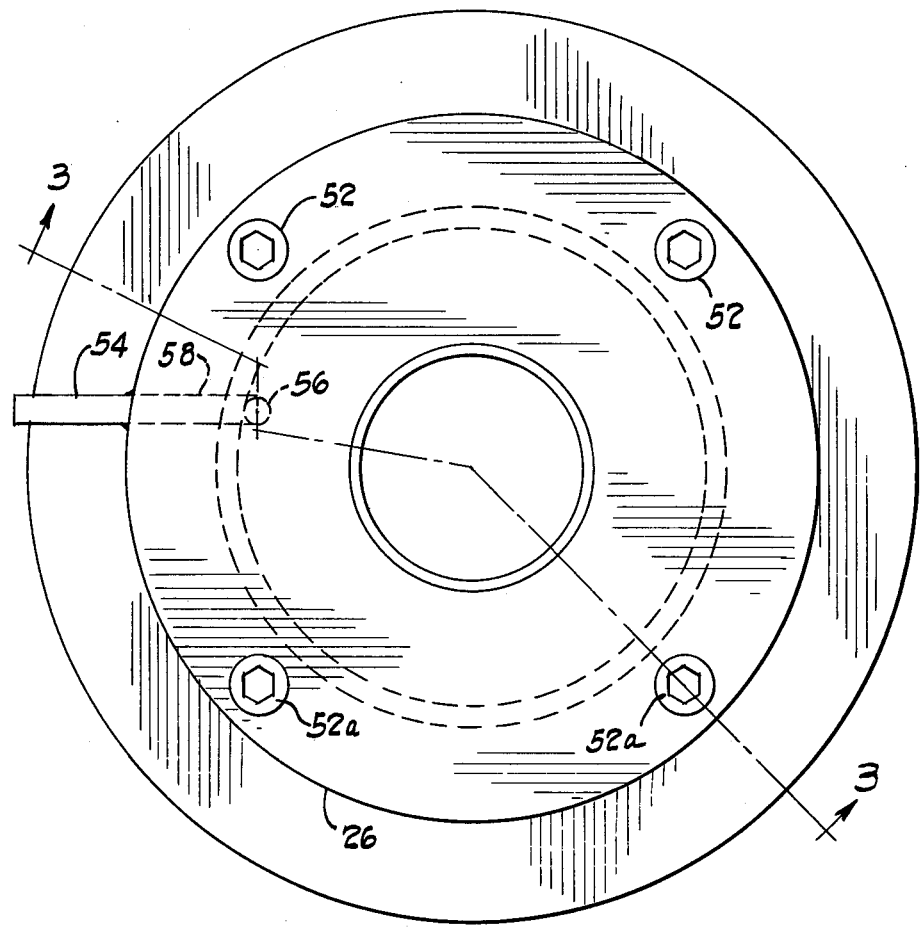
FIG. 4 is an end elevation view of the test head of FIG. 2.
Figure 5:
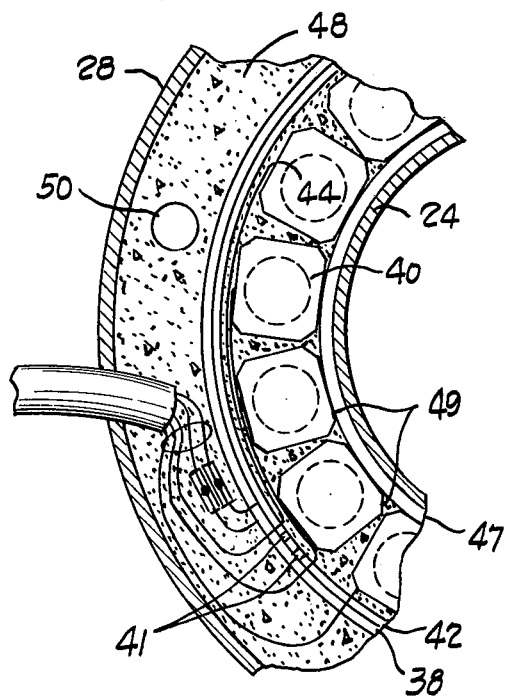
FIG. 5 is a cross sectional view, partly broken away, of the test head taken along the line 5—5 in FIG. 3.

Turning now to the drawings, FIGS. 1 and 2 show a pipe processing station 10 including pipe inspection apparatus embodying the present invention and comprising a series of roll stands 12 through which a hot pipe 14 passes soon after it has been fabricated. The station 10 is particularly suited for inspecting steel pipe at a temperature above its Curie temperature.

Inside the roll stands 12 at spaced locations along the pipe's length are fixed pipe guides 16, 16a for directing the pipe 14 along a path of travel. The guides 16, 16a are spaced apart to leave gaps 18 where drive rollers 20 contact the pipe and propel it through the inspection station 10.

An end pipe guide 16a positioned near an exit point of the station 10 (see FIG. 2) mounts an internal eddy current detector test head assembly 22. The test head 22 supports an eddy current excitation coil 38 and a number of detector coils 40 (FIGS. 2, 3, 5 and 8) in proximity to a pipe path of travel.

The detector coils sense variations in eddy currents in the pipe and correlate these variations to pipe flaw locations. These flaw locations are marked and if they occur too frequently corrective steps are taken in the pipe manufacturing procedure to reduce their incidence.

Figure 6:
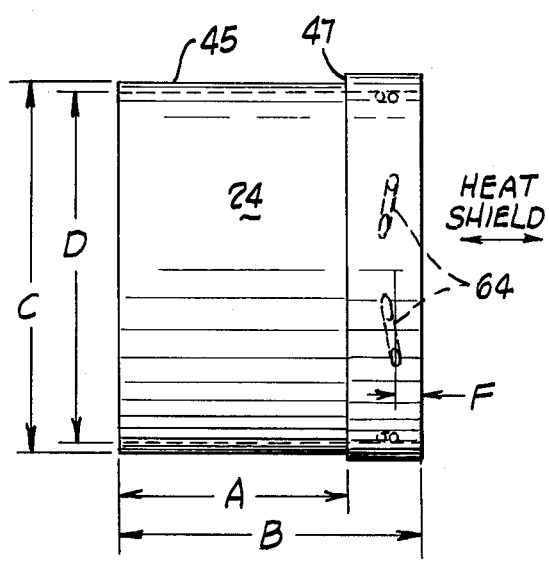
FIGS. 6 and 7 are detailed elevational and end views, respectively, of a portion of the test head of FIG. 3.
Figure 7:
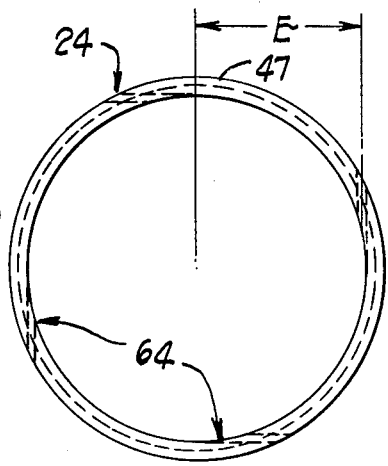
Figure 12:
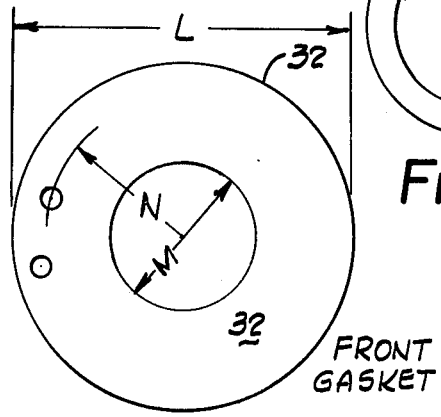
Figure 14:
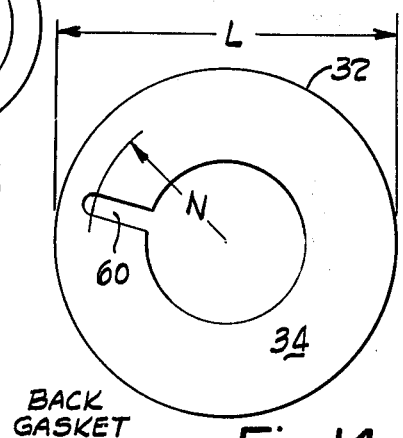

The test head 22 (FIG. 3) comprises a stainless steel heat shield 24, configured as a cylindrical sleeve having a small step defined by a lip 47 (FIGS. 6 and 7). The head also comprises body or housing structure including a cylindrical outer shell 28, and annular front 26 and back 30 plates which are also made of stainless steel. The back plate 30 is secured to the heat shield 24 and in the preferred embodiment this is accomplished by Heli-arc welding the back plate's inner surface to the heat shield's outer diameter. Interposed between the back plate 30 and the shell 28 and between the shell 28 and the front plate 26 are two neoprene rubber gaskets 32, 34. (See also FIGS. 12 and 14).

In combination, the heat shield 24, front and back plates 26, 30 and outer shell 28 define an annular chamber about the pipe path of travel in which are positioned the exciter coil 38 (see FIGS. 3 and 5) and the detector coils 40. The detector coils 40 are positioned radially inward with respect to the exciter coil which is wound around a cylindrical exciter coil form 42 made of plexiglass (see FIG. 3). Both the exciter coil and all the detector coils are cylindrically wound, with their axes positioned parallel to the travel path of the pipe.

Figure 13:
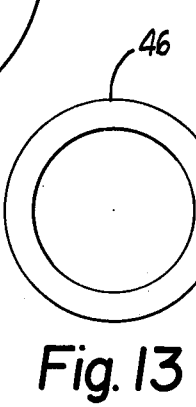

As a first step in assembly of the test head 22, each detector coil 40 is wound around a coil form 44 having square cross sectioned ends, and defining recessed cylindrically cross-sectioned intermediate portions about which the coil itself is wound. Each probe coil form bears terminals of known type forming interconnection points to which the probe coil ends are attached. These forms 44 are then positioned about a sleeve-like probe coil potting form (not shown) and glued at their ends to an annular probe coil assembly ring 46 (FIG. 13) which is positioned coaxial to the heat shield, and which is preferably also made of plexiglass. The potting form has an outside diameter equal to the outside diameter of the stepped portion (FIG. 6) defined by the lip 47 of the heat shield 24. The potting form helps position the probe coils 40 in relation to the heat shield. Probe coil interconnections are then made in known fashion and the exciter coil 38 and exciter coil form 42 are positioned around the detection coils 40. Leads to the probe coils 40 are threaded through access holes 41 drilled in the coil form 42 (FIG. 5) and protected with heat shrink tubing. The outer shell 28 is then positioned about the coils 38, 40 and the entire region from the inside of the shell 28 to the outside of the potting form is filled with a potting mixture 48. Once the potting mixture 48 has dried, the potting form is withdrawn from the interior of the assembly.

The withdrawal of the potting form leaves an unobstructed annular chamber 49 (FIG. 5) which is not filled with potting compound. The radial depth of the chamber 49 equals the height of the step on the heat shield defined by the lip 47 (FIGS. 6 and 7).

A hole or passageway 50 (FIGS. 3 and 5) is drilled longitudinally through the dry potting mixture. The potting mixture, detection coils, and exciter coil in combination comprise a potted assembly. The gaskets 32, 34 are then glued onto opposite ends of the potted assembly. The test head 22, thus assembled is inserted into the exit guide 16, and secured to the exit guide 16 by screws 52, 52a. A known source of energization is then connected to the excitation coil 38 and known detection circuitry is coupled to the probe coils 40.

Figure 8:
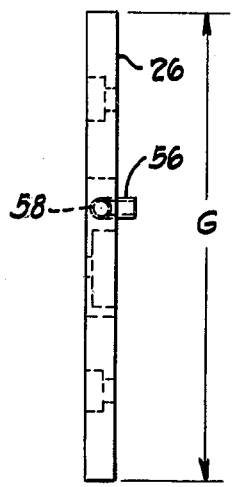
FIGS. 8–14 are detailed plan and elevation views of a number of components of the test head of FIG. 3.
Figure 9:
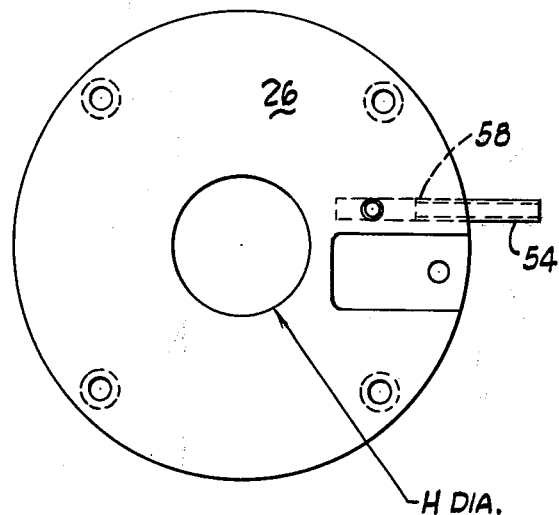
Figure 10:
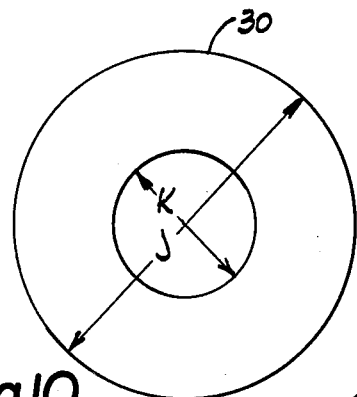
Figure 11:
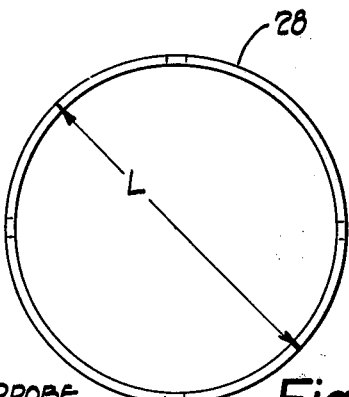

As seen most clearly in FIGS. 8 and 9, attached to the front plate 26 is an inlet fitting 54 and an outlet fitting 56 through which water or other suitable coolant may be transmitted to the test head 22. The inlet fitting 54 communicates with the outlet fitting 56 through a passageway 58 machined into the front plate 26. The rubber gasket 32 which contacts the front plate 26 includes a ¼" diameter hole, aligned in registration with the outlet fitting 56, through which the outlet fitting 56 extends to communicate in alignment with the passageway 50 which was drilled through the dry potting mixture 48.

The passageway 50 extends along the longitudinal dimension of the test head 22 and terminates at the back plate 30, by way of a slot-like passageway 60 (FIGS. 3 and 14) which is formed in the second rubber gasket 34. The passage 60 leads radially inward toward the pipe path of travel.

While both rubber gaskets 32, 34 define openings about the heat shield 24, it should be appreciated that the second of the two gaskets 34 has an inside diameter larger than the first gasket. Due to this larger inside diameter, the second passageway 60 terminates to define, with the shield, an annular space 62 which completely surrounds the stepped portion of the heat shield 24, and which communicates with the inlet fitting 54 on the front plate 26.

The three passageways 50, 58, 60 define an entrance path for water or other coolant to cool the test head 22 and, in a way described below, to remove foreign matter or debris from the space between the test head heat shield 24 and the pipe 14. Once the water (or other suitable coolant) has entered the annular space 62 surrounding the heat shield, it is forced through a series of apertures 64 which can be seen most clearly in FIGS. 6 and 7. These apertures are machined into the stepped portion of the heat shield and in the preferred embodiment comprise 1/16" holes extending to the interior heat shield surface in a direction nearly tangent to the interior surface to cause water passing through the apertures to immediately contact and disperse over the surface. The apertures 64 are also angled at about 80° from the workpiece path of travel, in the direction of the path, to give the water a modest longitudinal velocity component along the pipe movement direction and thus cause it to spiral about the inside surface of the shield (as shown by arrow Q in FIG. 3) until it exits the test head near the front plate 26.

While traversing the space between the pipe and the heat shield 24 the water dissipates heat buildup on the heat shield, which is caused by the heat shield's close proximity to the hot pipe 14. This tends to cool the coils 38, 40 and also remove debris which can adversely affect the coil's testing capability. Due to the tangential orientation of the apertures 64 combined with their angled orientation with respect to the pipe path of travel the water remains in contact with the heat shield 24 substantially without contacting the pipe 14. This path of water travel avoids substantial cooling of the pipe and thereby allows eddy current testing to be performed without use of a saturation coil.

The disclosed test head can be constructed for use with various diameter pipes. For use with other diameter pipes, it is possible that a different number or sizing of apertures 64 are preferably utilized to provide sufficient coolant flow rate (taking into account coolant viscosity and available pressure) to adequately cool the test head 22. The number of apertures chosen should be such that a spiralling sheet of water is produced along substantially the entire length of the heat shield 24. Tests have shown that four apertures 64, equally circumferentially spaced, are appropriate for many applications. More can be added to achieve the required water flow, as specified in more detail below.

Since the disclosed test head 22 has applicability for different sized pipes, the following table is disclosed to indicate various dimension parameters used in designing the test head 22 for different pipe. These parameters are labeled on the Figures and it should be appreciated that certain tolerances in these dimensions are acceptable in the practice of the invention. All dimensions are in inches.

| Parameter | Pipe Size | | | | |
|---|---|---|---|---|---|
| | ½ | ¾ | 1 | 1&¼ | 1&½ |
| A | 1.5 | 1.5 | 1.5 | 1.5 | 1.5 |
| B | 2.0 | 2.0 | 2.0 | 2.0 | 2.0 |
| C | 1.303 | 1.538 | 1.763 | 2.163 | 2.383 |
| D | 1.203 | 1.438 | 1.663 | 2.063 | 2.283 |
| E | .570 | .688 | .8 | 1.0 | 1.110 |
| F | 3/16 | 3/16 | 3/16 | 3/16 | 3/16 |
| G | 6.0 | 6.0 | 6.0 | 6.0 | 6&½ |
| H | 1.304 | 1.539 | 1.764 | 2.164 | 2.384 |
| I | 2.553 | 2.788 | 3.013 | 3.413 | 3.508 |
| J | 3.994 | 3.994 | 4.494 | 4.494 | 4.494 |
| L | 3.960 | 3.960 | 4.460 | 4.460 | 4.460 |
| M | 1.432 | 1.667 | 1.892 | 2.292 | 2.512 |
| N | 1&1/16 | 1&⅜ | 1&53/64 | 1&59/64 | 2.0 |

Certain empirically determined approximate minimum water flow rates are needed to generate a sheet of water along the heat shield's inner surface. In test heads 22 for scanning ½" or ¾" diameter pipe the minimum flow is 0.5 gallons per minute. For 1" diameter pipe, the minimum flow is 0.6 gallons per minute, and for 1¼" or 1½" diameter pipe, the minimum flow rate is 0.7 gallons per minute.

While a preferred embodiment of the invention has been disclosed in detail, various modifications or alterations may be made herein without departing from the spirit and scope of the invention set forth in the appended claims.

I claim:

1. Apparatus for testing a hot metallic workpiece movable along a path, said apparatus comprising:
    (a) a tubular shield having an inner surface surrounding the path and defining a passageway through which the workpiece can pass without contacting the shield said inner surface being exposed to face a workpiece as it traverses the passageway;
    (b) a detection unit mounted outside the shield for testing the workpiece as it passes through the shield passageway, and
    (c) structure including apertures defined in the shield for communication to a source of liquid coolant for flowing a liquid onto said inner surface of the shield at a direction oriented with respect to said surface for causing the fluid to flow across the inner surface of the shield and to flow off and drop away from a shield end substantially without contacting the workpiece.

2. A method for testing a hot metallic workpiece movable along a path utilizing a shield surrounding the path and defining a passageway through which the workpiece can pass without contacting the shield, said shield defining an inner surface exposed to a workpiece when traversing the passageway and a detection unit mounted outside the shield for testing the workpiece, said method comprising the steps of:
    (a) moving the workpiece along the path;
    (b) operating the detection unit to detect flaws in the passing workpiece, and
    (c) flowing a liquid onto a workpiece-facing surface of the shield at a direction oriented with respect to said surface for causing the fluid to flow across an inner surface of the shield and to drop from the shield when it reaches a shield end substantially without contacting the workpiece.

3. Apparatus for testing hot metallic pipe product which is moved longitudinally along a path, said apparatus comprising:
    (a) a shielding sleeve surrounding the path and configured and positioned for non-contacting movement of the pipe through the sleeve said shield having an inner surface directly exposed to the workpiece;
    (b) an eddy current detector unit mounted outside the sleeve for testing pipe moving through the sleeve, and
    (c) said sleeve defining ports in its walls adapted for communication with a source of fluid, said ports being oriented non-radially with respect to the pipe for directing liquid flow onto the interior surface of the shield without the fluid impinging on the pipe.

4. The apparatus of claim 3, further comprising:
    the ports in the sleeve being oriented to direct the liquid onto the inner surface of the sleeve at an angle substantially tangential to said inner surface.

5. The apparatus of claim 3, further comprising:
    said ports defined in said sleeve being angled to propel liquid effluent from said ports on to said inner surface with a velocity component in the direction of movement of said pipe.

6. A method for testing hot metallic pipe product moved longitudinally along a path, utilizing a shielding sleeve surrounding and directly facing the path and configured and positioned for non-contacting movement of the pipe through the sleeve, and an eddy current detector unit mounted outside the sleeve for testing pipe moving through the sleeve, said method comprising the steps of:
    (a) operating the eddy current detection unit for detecting flaws in the pipe moving through the sleeve, and (b) directing a coolant liquid non-radially with respect to the pipe onto the interior surface of the shield without the fluid impinging on the pipe.

7. The method of claim 6, wherein said directing step comprises:
discharging liquid onto the interior surface of the sleeve substantially tangentially with respect to that surface.

8. The method of claim 6, wherein said directing step comprises:
discharging said liquid onto said inner surface in a direction having a component extending in the direction of pipe movement.

9. An eddy current detector for inspecting a hot steel workpiece passing along a workpiece path of travel, the detector comprising:
(a) a body housing assembly having an inner tubular wall directly exposed to and facing the workpiece path and defining a central aperture surrounding the path and further defining an annular cross-sectioned chamber about the path and outside the inner tubular wall;
(b) detector coil apparatus supported within said chamber and outside the inner tubular wall to detect flaws in the workpiece as it moves along said path;
(c) said inner tubular wall defining a plurality of apertures adapted for communication with a source of a cooling liquid for directing said fluid onto said inner wall in a direction to cause the fluid to initially contact and cool the inner tubular wall and to subsequently flow from the inner wall substantially without contacting the workpiece.

10. The detector of claim 9 wherein said inner wall is cylindrical and wherein the workpiece comprises a portion of pipe.

11. An eddy current flaw detector system for inspecting hot steel pipe or the like passing along a workpiece path of travel, said system comprising:
(a) a pair of spaced annular end plate members;
(b) a substantially tubular, metallic, non-magnetic heat shield member surrounding and directly facing the workpiece path and carried by the end plates, said shield defining a set of outlet passages extending therethrough;
(c) a detector assembly including a probe coil fixed with respect to and located between the end plates and spaced outside the heat shield;
(d) an exciter connected to the detector assembly and positioned sufficiently close to the path to induce eddy currents in a workpiece;
(e) an outer shell enclosing the detector assembly and extending between the end plates; and
(f) said detector system including structure defining a passage extending through the volume defined by the inner tubular wall, end plates and outer shell and communicating with said outlet apertures for conducting liquid, said outlet passages being directed inward toward the workpiece path at a non-radial angle to cause said liquid to spiral in a sheet along the inner surface of the heat shield.

12. Eddy current flaw testing apparatus for detecting flaws in an elongated hot article as it is moved along a test path, said apparatus comprising:
(a) a body assembly having an apertured inner tubular wall surrounding and directly exposed to the test path, said body also defining a chamber about the test path and outside the inner tubular wall;
(b) structure within the chamber defining a longitudinally extending liquid conducting passage;
(c) a coil assembly including an exciter coil and a plurality of detector coils supported within said chamber, the coil assembly being mounted about at least a portion of the test path to detect distortions in a pattern of eddy currents induced in a workpiece, said detector coils being spaced radially inward from said exciter coil, and
(d) structure defined by the inner tubular wall, including a plurality of apertues therein, to direct a cooling liquid through said plurality of said apertures defined through said inner wall, each of said apertures being angled with respect to all radially inward directions with respect to the test path to cause said fluid to spiral about the article in said central aperture without substantially reducing said article's temperature.

13. A method of hot pipe flaw detection comprising the steps of:
(a) establishing a pipe path of travel;
(b) mounting an eddy current test head about said path, said test head including an excitation coil and a plurality of detector coils for detecting eddy currents induced by said excitation coil, said head further defining a cylindrical heat shield between and directly exposed to said path and said excitation and detector coils;
(c) energizing said excitation coil and monitoring output signals from the detector coils to establish the position of flaws in the pipe;
(d) directing a coolant liquid against the shield inner surface while avoiding substantial coolant contact with said pipe, and
(e) maintaining a flow path between said pipe and said shield to allow said coolant to flow along the shield's inner surface as the pipe passes said coils to sweep debris from space between the coils and the pipe and to subsequently exit from the shield region.

14. Apparatus for testing a hot workpiece relatively movable along a path with respect to said apparatus, said apparatus comprising:
(a) a shield member having a surface generally facing and directly exposed to the path and disposed proximate the path;
(b) a detection unit mounted opposite the shield with respect to the path for testing the workpiece as it moves along the path in the region of the shield, and
(c) structure couplable to a source of coolant for directing a coolant liquid onto said workpiece-facing surface of the shield at a direction oriented with respect to said surface for causing the fluid to flow upon and cool the shield and to subsequently flow off the shield substantially without contacting the workpiece.

15. The apparatus of claim 14, wherein:
said liquid flowing structure comprises structure for directing the fluid onto the shield surface substantially tangentially with respect to said surface.

16. The apparatus of claim 14, wherein:
said liquid flowing structure comprises structure for directing the liquid onto the shield surface with a component of motion extending in the direction of relative workpiece motion.

17. A method for testing a hot metallic workpiece movable along a path, utilitizing a shield having a surface directly facing the path and a detector unit mounted opposite the shield with respect to the path, said method comprising the steps of:
(a) moving the workpiece along the path relatively with respect to the shield;
(b) operating the detecting unit for testing the workpiece as it passes relatively with respect to the shield, and
(c) flowing a liquid onto the workpiece facing surface of the shield while the workpiece is passing the shield, said flow being in a direction oriented with respect to said surface for causing the liquid to flow across and exit from the region of the shield substantially without contacting the workpiece.

18. Apparatus for performing eddy current flaw testing on hot pipe movable along a path, said apparatus comprising:
(a) a heat shielding sleeve member surrounding said path and defining therethrough a plurality of apertures, each aperture being configured to direct fluid inwardly propelled through said aperture approximately tangentially with respect to the inner surface of the sleeve, and with a velocity component extending in the direction of pipe movement;
(b) a plurality of detector coils supported proximate but outside the shield and generally encircling the path;
(c) an exciter coil outside the detector coils and generally cylindrically wound and coaxial with the path;
(d) two apertured end plates mounted coaxially with respect to the shield on opposite sides of the exciter and detector coils;
(e) a generally cylindrical outer shell positioned cooperatively with respect to aid sleeve and end plates to enclose the exciter and detector coils in an annular cross sectioned chamber;
(f) an annular gasket interposed adjacent one of said end plates and said outer shell, said gasket being radially slotted to define a passage between said chamber and said apertures in the shielding sleeve;
(g) means defining a conduit within said chamber communicating between said slotted portion of said gasket and the exterior of said chamber for cooperating with a source of fluid coolant to deliver said coolant to be discharged onto the inner surface of the sleeve through said apertures.

19. A method of inspecting a steel pipe while heated to a temperature above the Curie point comprising:
(a) moving the hot pipe along a path of travel through a tubular eddy current type flaw inspection mechanism positioned at an inspection station and defining an inner tubular surface directly exposed to the path;
(b) directing a flow of liquid coolant into a pipe surrounding space between the pipe and the mechanism; and
(c) producing an encircling tube of liquid substantially completely spaced from but directly exposed to at least a part of that portion of the pipe in the inspection station while substantially completely covering an inner wall of a heat shield portion of the mechanism by use of both centripital and axially extending forces on the coolant as it is directed into the space.

20. The process of claim 19 wherein the axial force imparted to the coolant flow is imparted in the direction of pipe travel.

21. Apparatus for performing eddy current flaw detection testing on hot pipe movable along an axial path with respect to the pipe, said apparatus comprising:
(a) a heat shielding sleeve member defining an inner surface surrounding and directly exposed to said path, said sleeve having extending therethrough a plurality of apertures, each aperture being configured to direct liquid coolant inwardly propelled through said aperture and onto said inner surface approximately tangentially with respect to the inner surface of the sleeve, and with a velocity component extending parallel to said path;
(b) apparatus and circuitry located outside said sleeve member for inducing and detecting patterns of eddy current flow in a pipe portion moving along the path while passing through the sleeve member;
(c) means coupled to said apertures for communicating between said apertures and a source of liquid coolant for delivering liquid coolant to the inner surface of the sleeve member to discharge said coolant onto the inner surface of the sleeve to helically swirl about the sleeve inner surface substantially without directly contacting the pipe as it passes through the sleeve.

22. A method for performing eddy current flaw testing on hot pipe movable along a path axial with respect to said pipe, and utilizing a shielding sleeve member surrounding and directly exposed to said path, said method comprising the steps of:
(a) delivering liquid coolant to the inner surface of said sleeve facing the workpiece path to flow along said inner surface in a spiral manner to maintain coolant in contact with said inner surface but away from said path and said inspected pipe product substantially only by means of centrifugal force of said spirally flowing liquid coolant;
(b) inducing eddy current flow in a pipe passing along the path within the sleeve;
(c) detecting a characteristic of such eddy current flow, and
(d) interpreting said detected eddy current flow to provide indications in response to the passage of a workpiece flaw through the sleeve member.

* * * * *

UNITED STATES PATENT AND TRADEMARK OFFICE
CERTIFICATE OF CORRECTION

PATENT NO. : 4,461,995

DATED : July 24, 1984

INVENTOR(S) : Richard M. Harris

It is certified that error appears in the above-identified patent and that said Letters Patent is hereby corrected as shown below:

Column 6, line 26, change "38" to --58--.

Signed and Sealed this

Fifteenth Day of January 1985

[SEAL]

Attest:

GERALD J. MOSSINGHOFF

Attesting Officer

Commissioner of Patents and Trademarks